United States Patent [19]

Loeffler

[11] 4,202,355
[45] May 13, 1980

[54] X-RAY GRID ORTHOMETER

[76] Inventor: Cecil W. Loeffler, 912 E. Acacia, Hemet, Calif. 92343

[21] Appl. No.: 933,785

[22] Filed: Aug. 14, 1978

[51] Int. Cl.² .............................................. A61B 5/10
[52] U.S. Cl. ................................. 128/774; 33/174 D; 128/781
[58] Field of Search ............ 128/774, 781; 33/174 D, 33/170; 250/362, 456, 444, 515; 112/53

[56] References Cited
U.S. PATENT DOCUMENTS 3,520,293  7/1970  Atherholt .......................... 33/174 D

*Primary Examiner*—Willis Little
*Attorney, Agent, or Firm*—Clarence A. O'Brien; Harvey B. Jacobson

[57] ABSTRACT

An X-ray grid orthometer including a support having a generally horizontal surface over which is disposed a frame swingable from side-to-side relative to a fixed indicator which permits alignment of the frame with an X-ray tube of an associated X-ray machine. The frame can be in the form of a slide bearing, which includes a pair of substantially parallel slides separately mounted on associated slide guides for independent movement, and terminating in foot rests against which can be placed the legs of a person lying on the horizontal support surface in order to obtain an indication of leg length of the person, or the frame can be a four-link parallel-motion mechanism using a pair of parallel links in place of the slides. A weight bearing effect, also known as a spine-limb compression, can be achieved despite the prone position of the patient by use of a flexible element disposed about a pair of pulleys mounted on the support so as to permit the person whose leg lengths are being measured to pull with both hands and, thus, compress the feet thereof against plates of the foot rest. In this manner, visceral obstruction can be reduced by placing the subject in a supine position.

14 Claims, 9 Drawing Figures

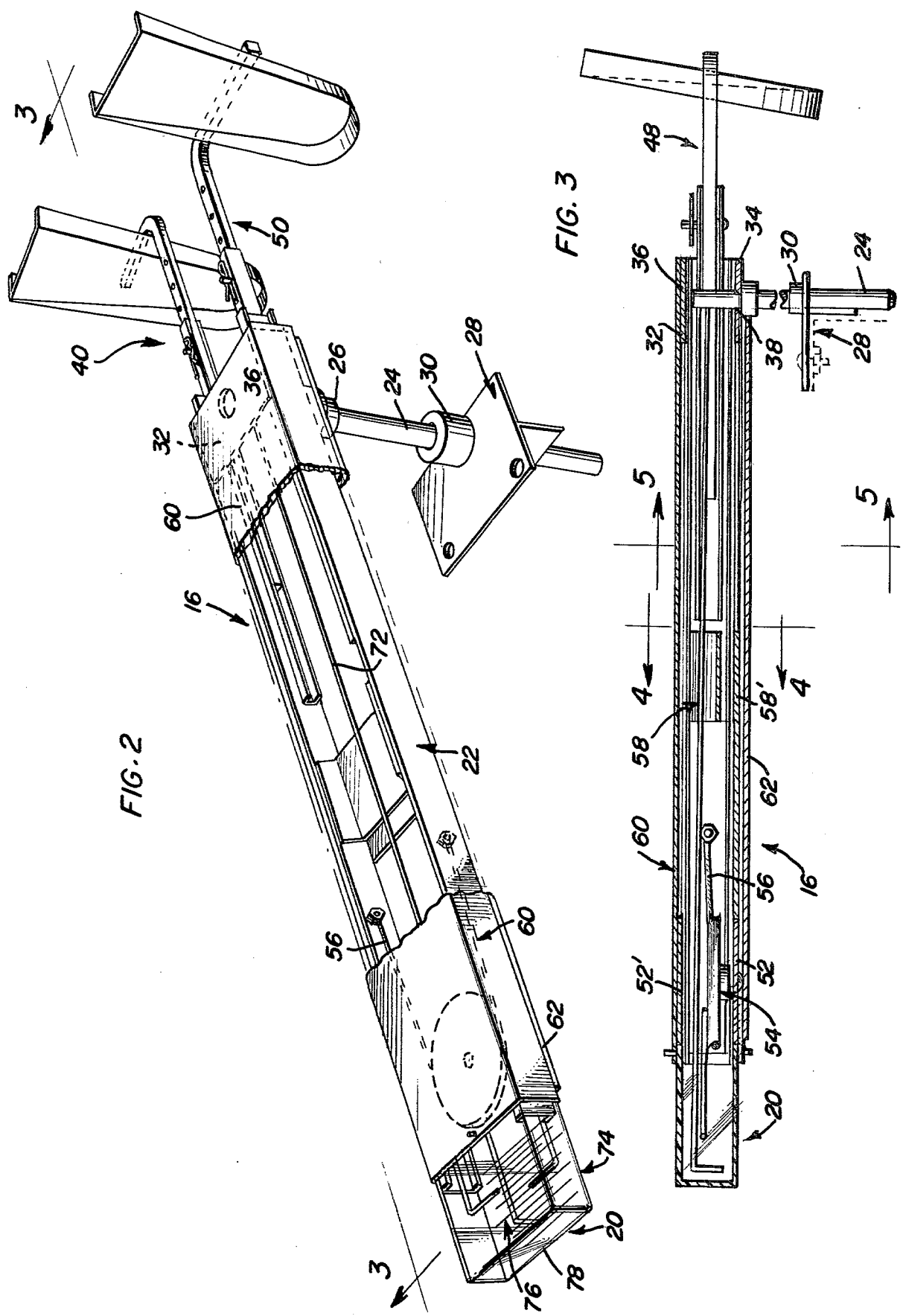

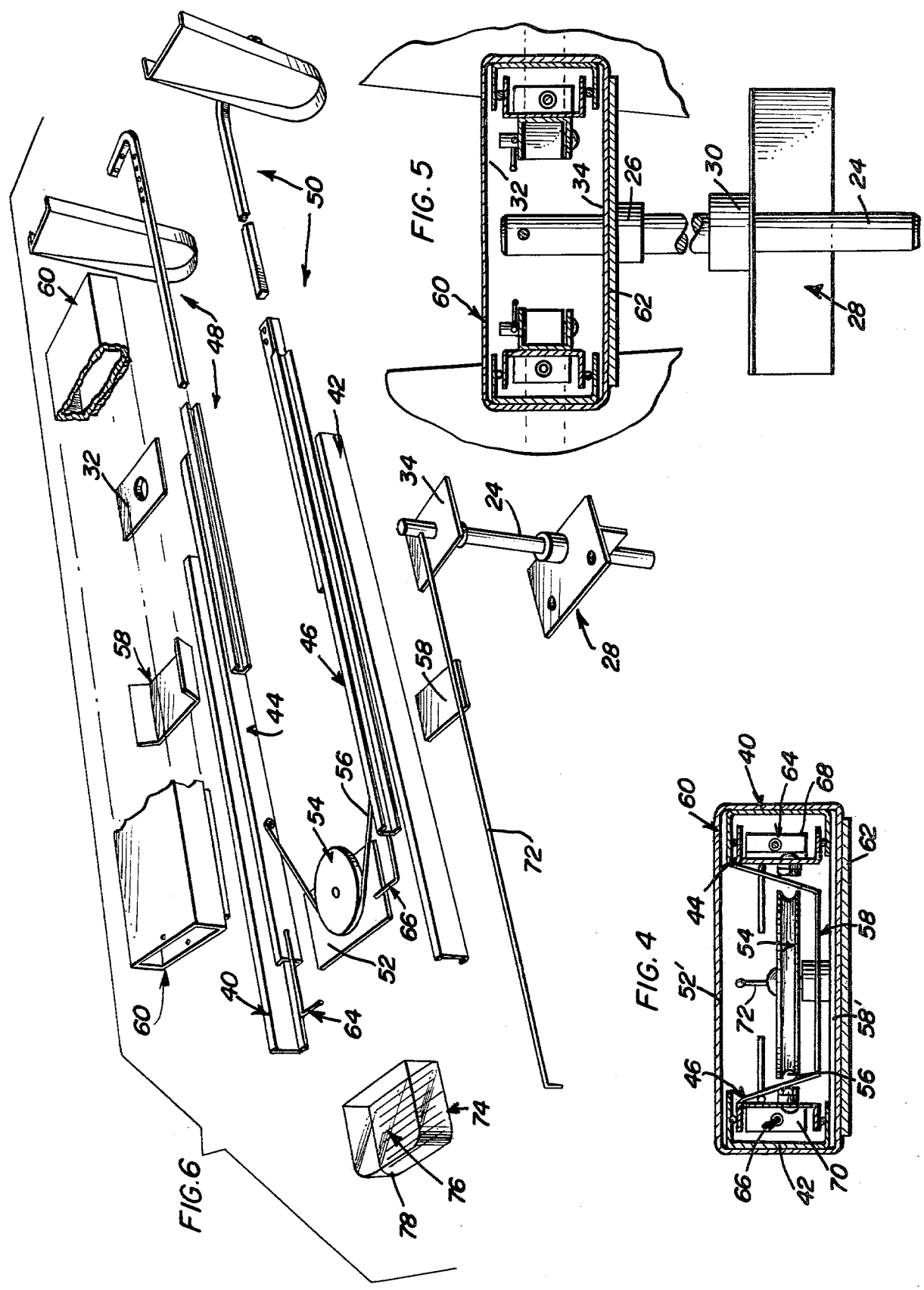

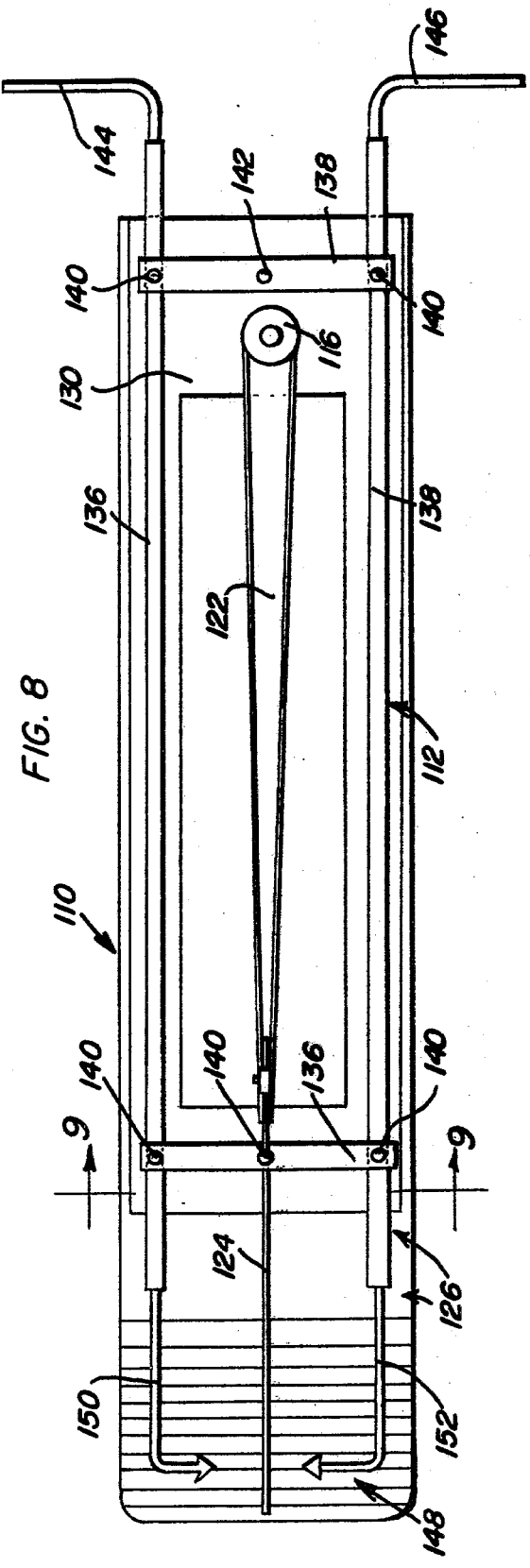
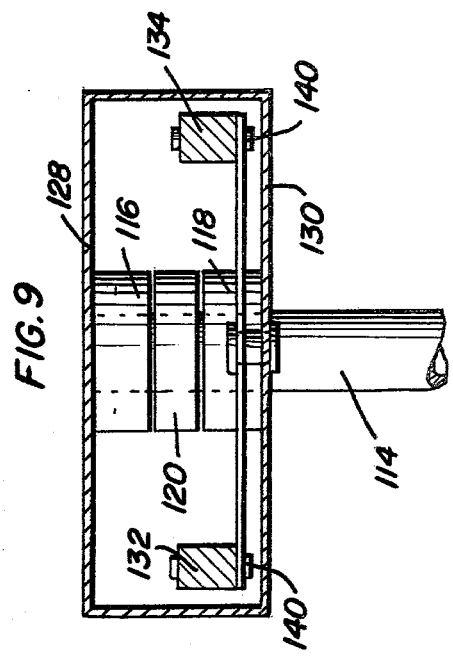
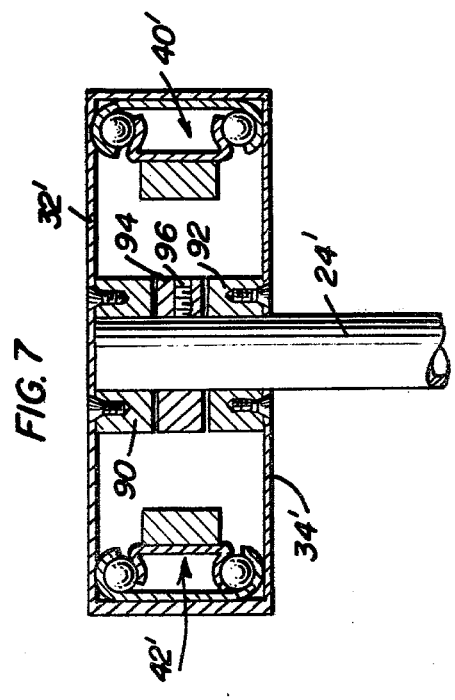

X-RAY GRID ORTHOMETER

BACKGROUND OF THE INVENTION

1. Field of the Invention

The present invention relates generally to a device that can be used for measuring the leg length of individuals that may have an anatomical leg length imbalance due to fracture, congential anomaly, or pelvic distortion (musle imbalance), and particularly to such a device which is capable of making desired leg measurements on persons in a supine position by closely approximating the conditions of a person standing upright.

2. Description of the Prior Art

Many medical practitioners have made it a practice to take pelvis-lumbar X-ray films of patients disposed in the upright or "posture" position, only to be disappointed in the quality of film obtained due to the gravitational pull on the abdominal viscera of the patient, giving an off-center picture if an anatomical imbalance is present. Further, the quality of the pictures obtained can be poor due to body movement of the patient. The measures usually taken to minimize the above problems only distort the ossious anatomy further, making the "posture" X-ray of questionable value. Therefore, many practitioners have abandoned the traditional posture film for the conventional supine position that will give better detail in the resulting pictures, but lacks the weight bearing effect, or spine-limb compression, obtained in a standing subject.

U.S. Pat. No. 2,712,696, issued July 12, 1955, to H. L. Johnson, discloses an example of a known pelvic leveling and leg measuring machine, while U.S. Pat. No. 3,520,293, issued July 14, 1970, to C. H. Atherholt, discloses an anthropometric apparatus particularly for actually measuring the length of legs, or for detecting legs of unequal length, of a subject in a supine position under conditions closely approximating those existing while a person is standing. The latter mentioned prior patent, U.S. Pat. No. 3,520,293, employs independently movable foot engaging members from applying force approximately one-half the weight of the person to each foot so as to duplicate the standing conditions. Further, U.S. Pat. No. 3,629,581, issued Dec. 21, 1971, to J. P. Smith, discloses a device for positioning a patient's shoulders during X-ray examination, wherein the patient pulls against the feet of the patient with both hands by means of a vertically disposed foot rest having attached thereto a pair of flexible elongated members engageable by the hands and wrist of the patient.

U.S. Pat. No. 2,349,664, May 23, 1944, to F. G. Leighty, discloses a frame for measuring body posture with the subject in a standing position, while U.S. Pat. Nos. 1,370,640, issued March 8, 1921, to A. Granger; 1,902,558, issued Mar. 21, 1933, to C. R. Johnson; 2,194,990, issued Mar. 26, 1940, to R. Torpin; 2,709,084, issued Apr. 23, 1957, to H. W. O'Dell et al; 3,723,743, issued Mar. 27, 1973, to D. D. Brackenbrough et al; and 3,974,388, issued Aug. 10, 1976, to W. Distler et al, disclose various examples of devices used for positioning a human torso, and/or protecting specific parts of the torso, during X-ray examination of the subject.

SUMMARY OF THE INVENTION

It is an object of the present invention to provide an X-ray grid orthometer which duplicates the weight-bearing effect, or spine-limb compression, of a subject in standing position while the subject is supine, thus reducing visceral obstruction, minimizing motion of the subject, and simultaneously registering any anatomical imbalance on the X-ray film with little obstruction, if any, of the radiographic record.

It is another object of the present invention to provide an X-ray grid orthometer which is compact in size and can be readily stored and transported.

Still another object of the present invention is to provide an X-ray grid orthometer which is convenient and simple to use, but which is capable of securing highly accurate results.

A still further object of the present invention is to provide an X-ray grid orthometer which is versatile in that it gives a direct readout of leg imbalance, and the like.

These and other objects are achieved according to the present invention by an X-ray grid orthometer having: a support; a frame mounted on the support for adjusting to the length of the leg of a subject; and an indicator arrangement mounted on the support and slide assembly for registering an imbalance of the length of the legs of the patient. Perferably, the support includes a horizontal surface on which the subject can lie in a supine position, with the frame including either a linear slide bearing or a four-link parallel-motion mechanism arranged substantially horizontally over the surface of the support and bearing pivotally mounted on the support for swinging movement about a substantially vertical axis.

The frame further includes a post mounted on the support in substantially vertical orientation arranged extending above the horizontal surface of the support. A clamping arrangement adjustably mounts on the post for supporting the frame, while a bracket is secured to the post vertically below the clamp arrangement for mounting the post on the support.

One embodiment uses a slide bearing which advantageously comprises a pair of spaced, substantially parallel, coextensive, stationary slide guides affixed to the support, with a pair of slides mounted on the slide guides, one of the slides to a respective one of the guides. A pair of foot rests are adjustably mounted on the slides, with each of the foot rests including a plate against which a foot of the subject being measured can be placed in abutting relationship.

A second embodiment uses a four-link parallel-motion mechanism with a parallel pair of the links being disposed coextensively with the extent of a patient, and the entire mechanism being disposed in a sheath suitably mounted on the post as described above, with the mechanism being pivotally mounted to the sheath, or more specifically to cross members thereof, in order to permit the desired parallel movement of the longitudinally extending side links of the mechanism.

The indicator arrangement preferably includes a pair of movable anatomical indicators mounted on the frame in spaced relation from the foot rests, so as to be adjacent the head of a subject, and a stationary centering indicator mounted on the support adjacent the foot rests and extending coextensively with the parallel slides or links. An indicator member in the form of a transparent housing is mounted on the frame adjacent the movable anatomical indicators, and is provided with indicia forming a grid calibrated for direct reading of a leg imbalance. Further, a mark is preferably provided on the housing for centering the frame with respect to the stationary central indicator, and with the center beam indicator of an associated X-ray tube.

A pair of pulleys are mounted on the support in spaced relation to one another on either side of the frame and adjacent the point of pivotal mounting of the frame to the support. A flexible, elongated member having end portions is disposed about the pulleys, and arranged so as to be engageable at the end portions thereof by a person whose legs lengths are being measured for compressing the lumbar spine and legs of the subject by the latter pulling with both hands on the flexible member, thus compressing the feet of the subject against the plates of the foot rests.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 2 is an enlarged, perspective view, partly broken away and in section, showing from the reverse direction the grid orthometer seen in FIG. 1.

FIG. 3 is a fragmentary, sectional view taken generally along the line 3—3 of FIG. 2.

FIG. 4 is an enlarged, sectional view taken generally along the line 4—4 of FIG. 3.

FIG. 5 is an enlarged, fragmentary, sectional view taken generally along the line 5—5 of FIG. 3.

FIG. 6 is a fragmentary, exploded, perspective view showing the various parts of the grid orthometer seen in FIGS. 1 through 5.

FIG. 7 is a sectional view similar to FIG. 5, but showing a modified mounting arrangement of the first embodiment of the invention.

FIG. 8 is a schematic, top plan view showing a second embodiment of the invention.

FIG. 9 is an enlarged, sectional view taken generally along the line 9—9 of FIG. 7.

DESCRIPTION OF THE PREFERRED EMBODIMENT

Figure 1:
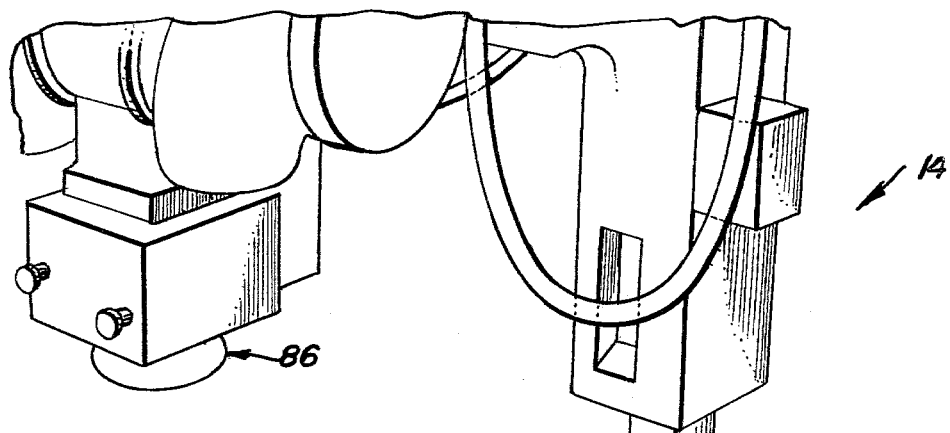
FIG. 1 is a fragmentary, schematic, perspective view, partly cut away and in section, showing an X-ray grid orthometer according to the present invention in use for taking X-ray pictures of the pelvic area of a subject.
Figure 1:
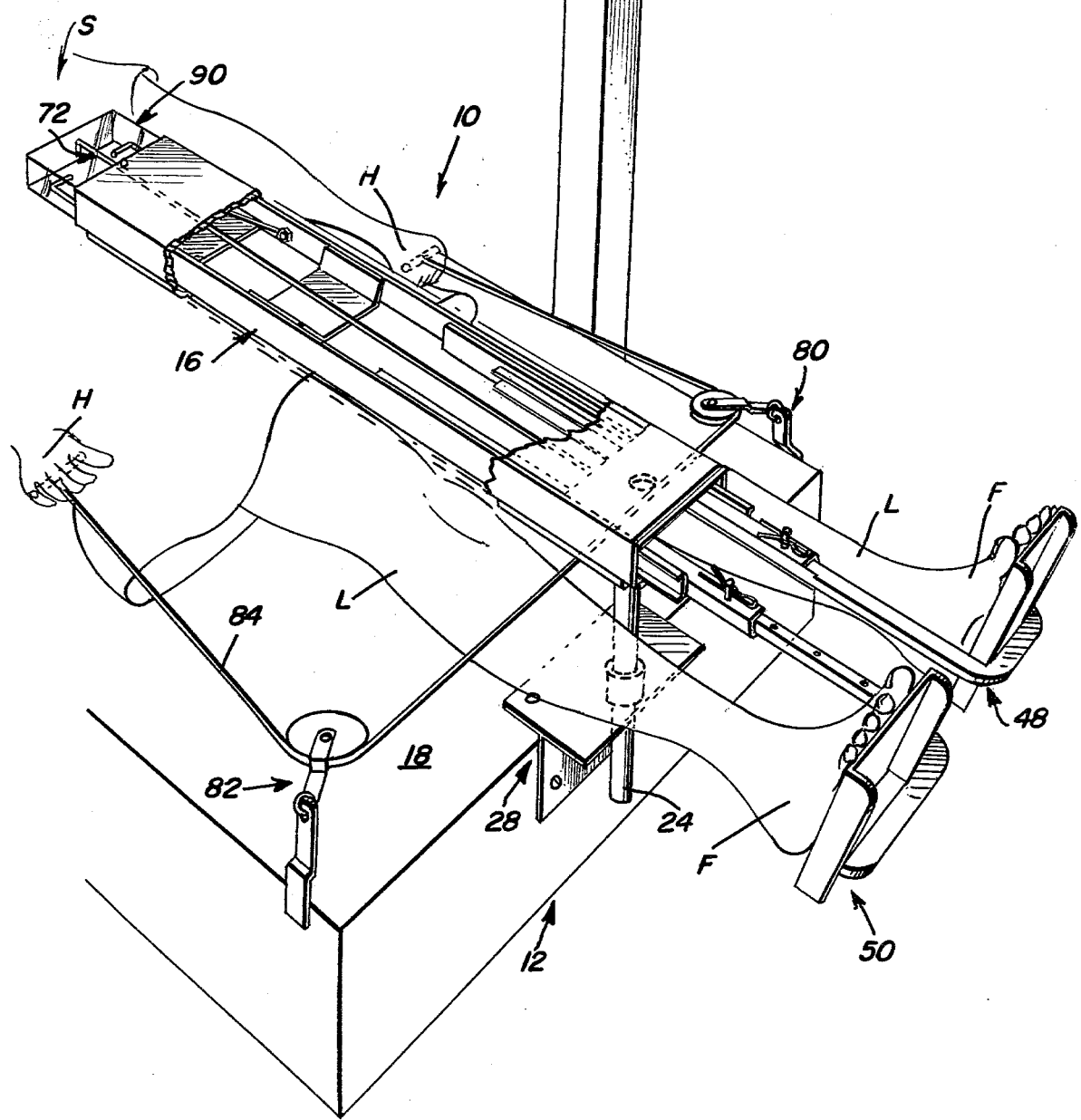

Referring now more particularly to FIG. 1 of the drawings, an X-ray grid orthometer 10 according to the present invention is illustrated as mounted on a support in the form of a table 12 disposed adjacent to a conventional X-ray machine 14 so as to place the horizontal surface directly beneath an X-ray tube portion of machine 14. Since the general arrangement of table 12 and machine 14 as illustrated in FIG. 1 is of a conventional nature, it will not be described in greater detail herein.

Orthometer 10 includes a slide assembly 16 mounted on table 12 for adjusting to the length of the leg of a subject S disposed in supine position on a substantially horizontal, planar surface 18 forming the top of table 12. An indicator arrangement 20 is mounted on table 12 and slide assembly 16 for registering an imbalance of the length of the legs L of the subject S in a manner to be described below.

Referring now more particularly to FIGS. 2 through 6 of the drawings, slide assembly 16 includes a linear slide bearing 22 arranged in a substantially horizontal orientation over surface 18 of table 12. This slide bearing 22 is pivotally mounted on table 12 for swinging movement about a substantially vertical axis by a post 24 mounted on table 12 in substantially vertical orientation and arranged extending above horizontal surface 18 of table 12. A clamp in the form of collar 26 having a set screw (not shown) or other clamping device provided thereon is adjustably mounted on post 24 for supporting the slide bearing 22, while a bracket 28 is secured to post 24, as by a collar 30 similar in construction to collar 26, for mounting post 24 on the upper edge of table 12 which will be adjacent the feet of a subject S being measured and X-rayed. Cross members 32 and 34 each provided with an associated hole 36 and 38 are received on post 24 and are attached to bearing 22 for mounting bearing 22 on post 24, with the lowermost cross member 34 resting on the upper surface of the clamp collar 26.

Slide bearing 22 comprises a pair of spaced, substantially parallel, coextensive, stationary slide guides 40 and 42 affixed to post 24, and hence table 12, cantilever-fashion by the cross members 32 and 34 being affixed to flange portions of the generally channel-shaped guides 40 and 42. A pair of slides 44 and 46 are slidably mounted on the slide guides 40 and 42, with one of the slides 44 and 46 to a respective one of the guides 40, 42. A pair of foot rest assemblies 48 and 50 are mounted on the slides 44 and 46 for receiving the feet F of subject S (FIG. 1), with each of these assemblies 48 and 50 including a foot plate having a shaft extending therefrom and slidably received in a channel affixed to the associated one of the slides 44 and 46. Cotter pins, and the like, can be employed for engagement in apertures so provided in the channel and shafts for retaining the foot rests in a desired position for a person of a given height.

A cross member in the form of a pulley support 52 extends between the slide guides 40 and 42 in the lower portion thereof and in longitudinally spaced relation to the cross members 32 and 34 for journalling thereon a pulley 54. A cable 56 has ends attached to the respective slides 44 and 46 and is arranged engaging pulley 54 for being guided thereby and maintaining a preset relationship between the slides 44 and 46. A generally U-shaped cross member 58 is disposed between the slides 44 and 46 midway the length thereof for assuring proper spacing of the slides 44 and 46 from one another, and for rigidifying the slide bearing 22. A cover 60 in the form of a longitudinally extending sheath is disposed over slide bearing 22 along the entire length of the guides 40 and 42 for enclosing the bearing 22, while a sheet or layer 62 of an insulation material, such as lead, covers the undersurface of cover 60 to function as a gonad shield for a person being measured and X-rayed.

The indicator arrangement 20 includes a pair of movable anatomical indicators 64 and 66 mounted on the slides 44 and 46, respectively, in longitudinally spaced relation from the foot rest assemblies 48 and 50. Guide blocks 68 and 70 are disposed in the associated ends of the slides 44 and 46, and are provided with centrally disposed through bores which mountingly receive the wire-like indicators 64 and 66. A centering indicator 72 is mounted on post 24, so as to be disposed adjacent the foot rest assemblies 48 and 50, which indicator 72 extends coextensively with the slide guides 40 and 42. An indicator member in the form of a transparent housing 74 is mounted on the slide guides 40 and 42 adjacent the movable anatomical indicators 64 and 66, and is provided with appropriate indicia 76 forming a grid calibrated for direct reading of leg imbalance. Further, X-ray pictures are taken through housing 74, so that indicia 76, in cooperation with the indicators 64 and 66, can form a permanent record of the leg imbalance on the film. A mark 78 is provided on the head of housing 74 for facilitating alignment of indicator 72 with the center of the slide bearing 22.

Referring again to FIG. 1 of the drawings, a pair of pulley assemblies 80 and 82 are mounted on table 12 in spaced relation on either side of the slide bearing 22 and adjacent the point of pivotal mounting thereof to post 24. Disposed about these pulleys 80, 82 is a flexible, elongated element 84 having end portions engageable by a subject S whose leg lengths are being measured for compressing the lumbar spine and the legs of the person.

In operation, and again referring to FIG. 1, the supine position is utilized to record leg measurements by placing the subject S in a supine position on surface 18 of table 12. The subject grasps the ends of member 84 in hands H so as to compress feet F of the subject S against the plates of the foot rest assemblies 48 and 50. Subject S can view only the X-ray grid orthometer centering indicator 72 and the, for example, translucent line forming mark 78 on the head of housing 74. This will minimize any inaccuracy which might arise due to suggestive or willful distortions of the subject S while measurements are being made. When equal pressure is applied to the plates of the foot rest assemblies 48 and 50 by pulling on the handle or end portions of element 84, the stationary indicator 72 will be positioned in the center of the indicator housing 74. If there is any anatomical imbalance or any unequal leg length, it will register on the movable anatomical indicators 64 and 66. This imbalance is determined by the position of the indicators 64 and 66 on the grid form by inidicia 76 of housing 74. Photographing with an X-ray machine 14 through the housing 74 will record the results of the measurements in the form of a permanent record.

The indicia 76, which can be constructed from a suitable metal, can be calibrated at, for example, one centimeter apart.

Referring now more particularly to FIG. 7, the slide bearing as employed with the embodiment of FIGS. 1 through 6 can employ a pair of ball-bearing slides 40' and 42' of generally conventional construction, with the entire slide bearing being mounted on a post 24' by attachment of upper and lower bearings 90 and 92 to upper and lower cross plates 32' and 34', respectively. Disposed on post 24' between the bearings 90 and 92 is a collar 94 used to support the central indicator and secureable to post 24' as by the illustrated set screw 96. It will be appreciated that the modified embodiment illustrated in FIG. 7 will function in substantially the identical manner as the embodiment of FIGS. 1 through 6 described above.

FIGS. 8 and 9 illustrate a second basic embodiment of the invention in which an orthometer 110 employs in place of the slide bearings described above a four-link parallel-motion mechanism 112. This mechanism is secured to a substantially vertical post 114, similar to post 24 and 24', in a manner similar to the mounting of the modified embodiment shown in FIG. 7, with an upper bearing 116 and a lower bearing 118 bracketing a collar 120 which merges into an arm 122 on which the central indicator 124 is affixed. A cover 126 can be arranged shrouding mechanism 112, which cover 126 is partially formed in a suitable manner by the illustrated top plate 128 and bottom plate 130. Bearings 116 and 118 are secured to plates 128 and 130, respectively, for swingably mounting the mechanism 112 for movement in a substantially horizontal plane above the surface of a table, not shown.

Mechanism 112 includes a substantially parallel pair of links in the form of the longitudinal extending rails 132 and 134, with the other pair of links of mechanism 112 being in the form of levers 136 and 138 connected to end portions of rails 132 and 134 as by conventional pins 140, and themselves pivoted mounted on the bottom plates 130 as by pins 142.

A pair of foot supports or rests 144 and 146 are secured to respective, adjacent end portions of the rails 136 and 138 so as to function in the manner of the foot rests 48, 50. Arm 122 which supports indicator 124 can be constructed of sheet metal, and the like, so as to have upturned flanges connected together by a supporting web.

At the head end of mechanism 112, there is attached as to cover 126 a transparent housing 148 constructed in the identical manner as housing 74, with a pair of indicators 150 and 152 being attached to and arranged extending parallel from those end portions of rails 136 and 138 disposed adjacent to housing 148.

As will be appreciated, the embodiment of the invention as illustrated in FIGS. 8 and 9 will function in the identical manner as the basic embodiment of the invention shown in FIGS. 1 through 7.

As can be readily understood from the above description and from the drawings, an X-ray grid orthometer according to the present invention permits utilization of the supine position to record leg measurements, distortion due to spine erector muscle spasm or contracture thus being minimized. Grid interference of radiograph detail is minimal, the housing 74, 148 being constructed from a radiolucent material, and the orthometer can be used for student training or research as well as clinical practice. By taking before and after readings, the spinal manipulator (chiropractor or osteopath) can record the amount of pelvic distortion and degree of correction. As stated above, the readout can be recorded directly or as a permanent record on a radiograph. The orthometer also functions as a male gonad radiation shield when provided with the insulating layer 62. Further, the foot rest assemblies 48 and 50 can be modified in a known manner to be used to fit heel and sole lifts as a measurement for the built up shoe, or for the fitting of artificial limbs.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An X-ray grid orthometer, comprising, in combination:
    (a) frame means mountable on a support for adjusting to the length of the legs of a subject being measured for leg imbalance;
    (b) indicator means mountable on the support and mounted on the frame means for registering balance and imbalance of the legs of a subject, wherein the frame means includes a linear slide bearing arranged substantially horizontally over a horizontal surface of the support, the slide bearing being pivotally mountable on the support for swinging movement about a substantially vertical axis to enable centering of said frame with respect to said support.

2. A structure as defined in claim 1, wherein the indicator means include a stationary indicator, and the frame means further includes a post mountable the support in substantially vertical orientation and arranged extending above the horizontal surface of the support, bearing means adjustably mounted on the post for supporting the slide bearing cantilever-fashion, with the indicator means including a collar mounted on the post and affixed thereto for supporting cantilever-fashion the stationary indicator of the indicator means.

3. A structure as defined in claim 1, wherein the slide bearing comprises, in combination:
(1) a pair of spaced, substantially parallel, coextensive, stationary slide guides affixable to the support;
(2) a pair of slides mounted on the slide guides, one of the slides to a respective one of the guides; and
(3) a pair of foot rest means mounted on the slides for providing abutment surfaces for the feet of a subject whose legs are being measured.

4. A structure as defined in claim 3, wherein the frame means further includes a post mountable on the support in substantially vertical orientation and arranged extending above the horizontal surface of the support, clamp means adjustably mounted on the post for supporting the slide bearing cantilever-fashion, and bracket means secured to the post vertically below the clamp means for mounting the post on the support.

5. A structure as defined in claim 4, wherein the indicator means includes a pair of movable anatomical indicators mounted on the slides in spaced relation from the foot rest means, a stationary centering indicator mounted on the support adjacent the foot rest means and extending coextensively with the slide guides, and an indicator member mounted on the slide guides adjacent the movable anatomical indicators and provided with indicia forming a grid calibrated for reading of a leg imbalance.

6. A structure as defined in claim 5, wherein the indicator member includes a transparent housing affixed to the slide guides, the indicia being provided on the housing, with the frame means further including a pulley, and a cable engaging the pulley for being guided thereby and connected to the slides for maintaining a relationship between the slides.

7. A structure as defined in claim 6, further including a pair of pulleys mountable on the support in spaced relation on either side of the frame means and adjacent the point of pivotal mounting of the slide means to the support, and a flexible, elongated element having end portions and disposed about the pulley assemblies, and engageable at the end portions by a subject whose leg lengths are being measured for compressing the lumbar spine and the legs of the subject.

8. An X-ray grid orthometer, comprising, in combination:
(a) frame means mountable on a support for adjusting to the length of the legs of a subject being measured for leg imbalance;
(b) indicator means mountable on the support and mounted on the frame means for registering balance and imbalance of the legs of a subject, wherein the indicator means includes a pair of anatomical indicators mounted on the frame means, a stationary centering indicator mountable on the support and extending parallel to and substantially coextensive with the anatomical indicators, and an indicator member mounted on the frame means adjacent the movable anatomical indicators and provided with indicia forming a grid calibrated for reading of a leg imbalance.

9. An X-ray grid orthometer, comprising, in combination:
(a) frame means mountable on a support for adjusting to the length of the legs of a subject being measured for leg imbalance;
(b) indicator means mountable on the support and mounted on the frame means for registering balance and imbalance of the legs of a subject, wherein the frame means includes a four-link parallel-motion mechanism arranged substantially horizontally over a horizontal surface of the support, the mechanism being pivotally mountable on the support for swinging movement about a substantially vertical axis to enable centering of said frame with respect to said support.

10. A structure as defined in claim 9, wherein the indicator means includes a stationary indicator and the frame means further includes a post mountable on a support in substantially vertical orientation and arranged extending above a horizontal surface of the support, bearing means adjustably mounted on the post for supporting the mechanism cantilever-fashion, with the indicator means including a collar mounted on the post and affixed thereto for supporting cantilever-fashion the stationary indicator of the indicator means.

11. A structure as defined in claim 10, wherein the indicator means further includes a pair of anatomical indicators mounted on the frame means, the stationary indicator arranged substantially parallel to and substantially coextensive with the anatomical indicators, and an indicator member mounted on the frame means adjacent the movable anatomical indicators and provided with indicia forming a grid calibrated for reading of a leg imbalance.

12. A structure as defined in claim 11, wherein the indicator member includes a transparent housing affixed to the frame means, the indicia being provided on the housing.

13. An X-ray grid orthometer, comprising, in combination:
(a) frame means mountable on a support for adjusting to the length of the legs of a subject being measured for leg imbalance;
(b) indicator means mountable on the support and mounted on the frame means for registering balance and imbalance of the legs of a subject, further including a pair of pulleys mountable on the support in spaced relation from one another on either side of the frame means, and a flexible, elongated element having end portions and disposed about the pulleys and engageable at the end portions by a subject whose leg lengths are being measured for compressing the lumbar spine and the legs of the person.

14. A method for measuring the leg length of individuals that may have anatomical leg length imbalance due to any one of fracture, congenital anomaly, and pelvic distortion, comprising the steps of:
(a) placing the patient in a substantially horizontal position with the feet thereof abutting supports; positioning a horizontally swinging frame which supports the feet abutting supports over and extending parallel to the subject; and aligning a stationary indicator with the frame, a center line of a supporting table, and with a center beam indicator of an X-ray tube;

(b) simulating a weight-bearing effect on the lumbar spine and legs of the patient by having the patient pulling with both hands against the feet abutting supports;

(c) measuring the relative position of each of the feet abutting supports.

* * * * *